United States Patent [19]

Dysarz

[11] Patent Number: 5,045,081
[45] Date of Patent: Sep. 3, 1991

[54] TRAP IN BARREL ONE HANDED RETRACTABLE VIAL FILLING DEVICE

[76] Inventor: Edward D. Dysarz, 11423 Triola La., Houston, Tex. 77072

[21] Appl. No.: 568,879

[22] Filed: Aug. 17, 1990

Related U.S. Application Data

[63] Continuation-in-part of Ser. No. 466,722, Jan. 16, 1990, Pat. No. 4,973,316.

[51] Int. Cl.$^5$ .............................................. A61B 19/00
[52] U.S. Cl. .................................... 604/411; 604/905; 141/329; 141/383
[58] Field of Search ...................... 604/205, 86, 89, 90, 604/88, 201, 411, 415, 403, 414, 905; 141/18, 19, 329, 330, 369, 372, 383

[56] References Cited

U.S. PATENT DOCUMENTS

| 4,576,211 | 3/1986 | Valentini et al. | 141/329 |
| 4,798,605 | 1/1989 | Steiner et al. | 604/411 |
| 4,935,020 | 6/1990 | Broden | 604/411 |

Primary Examiner—John D. Yasko

[57] ABSTRACT

A vial filling device having a needle cannula fixed to a slidable piston. The slidable piston is held within an elongated hollow barrel by an open spring and latch means. When the elongated hollow barrel is attached to the vial assembly, a lap flange is forced open and the slidable piston is pressed with a thumb, forcing the spring to compress and forcing the needle cannula to penetrate the soft plug in the vial. The blood or other fluid flows through the needle cannula until sufficient blood or other fluid is in the vial. When the vial is suitably filled, the thumb is removed from the slidable piston and the spring pushes the slidable piston in a direction away from the vial thus removing the needle cannula from the vial plug and holding the needle cannula safely inside of the elongated hollow barrel. The elongated hollow barrel is further removed from the plug, the lap flange closes thus enclosing the contaminated needle cannula.

9 Claims, 5 Drawing Sheets

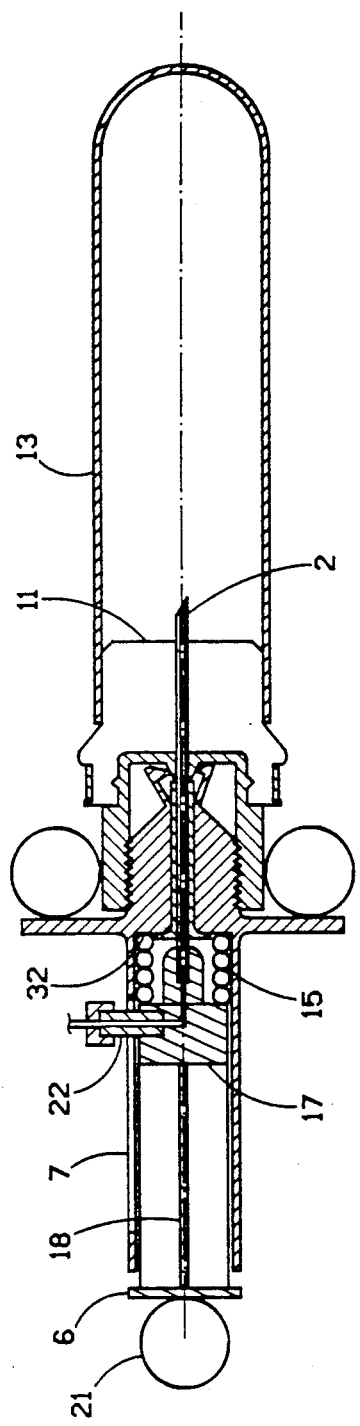
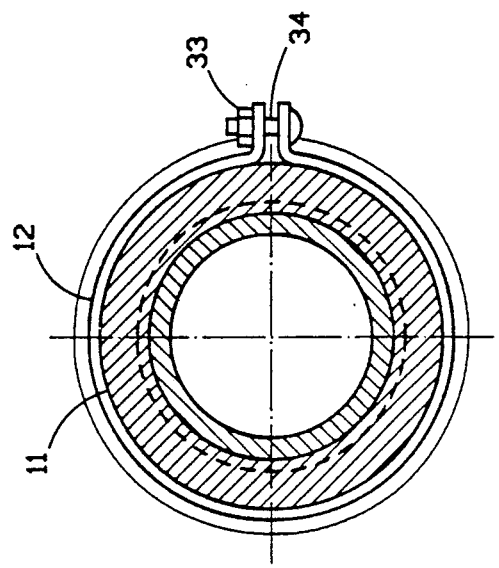
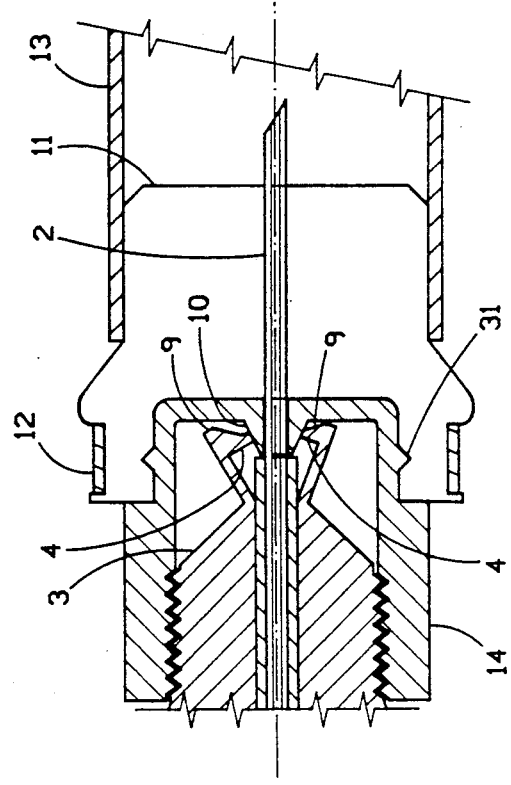
FIGURE 4
FIGURE 6
FIGURE 5

TRAP IN BARREL ONE HANDED RETRACTABLE VIAL FILLING DEVICE

BACKGROUND OF THE INVENTION

There are several types of safety vial filling designs available today. One such design is shown in a patent issued to JAGGER et al on June 3, 1986 U.S. Pat. No. 4,592,744. This is a safety blood sampling device, however, it requires two (2) hands to operate or to cover the needle cannula.

Blood sampling devices and vial filling devices are similar to syringes and there are many safety syringes available. Some of these designs have a sleeve or sheath that will cover the needle after it has been used. Some typical designs with sleeves or sheaths are Z. M. ROEHR et al U.S. Pat. No. 3,008,570, Z. M. ROEHR U.S. Pat. No. 3,107,785, BARTNER, et al U.S. Pat. No. 3,895,633, GK BURKE U.S. Pat. No. 3,306,291, GYURE et al U.S. Pat. No. 4,300,678, WINSTEAD HALL U.S. Pat. No. 4,356,822, SAMPSON U.S. Pat. No. 4,425,120, LARSON U.S. Pat. No. 4,639,249, HARBAUGH U.S. Pat. No. 4,655,751, STRAUSS U.S. Pat. No. 4,664,654, BRAGINETZ U.S. Pat. No. 466,435, SPENCER U.S. Pat. No. 4,702,738, MILORAD U.S. Pat. No. 4,702,739, SPENCER U.S. Pat. No. 4,801,295, PONCY U.S. Pat. No. 4,816,022, and HUGHES U.S. Pat. No. 4,840,619.

Other designs have a retractable needle such as WELTMAN U.S. Pat. No. 3,306,290, and DENT U.S. Pat. No. 4,392,859. These designs do not have a means whereby the needle is extended from the syringe and held in place in a positive and rigid position in order to first inject the needle prior to injecting the medication. Still other designs have methods of bending the needle to render it harmless after the medication has been injected Most of these designs have one major purpose and that is to prevent the spread of infectious diseases such as aids, hepatitis, or other diseases from an accidental injection with a contaminated needle into others after the needle of the syringe was inserted into a patient with the above mentioned disease. These various designs all work well to a degree, but they all fall short of their intended purpose during the act of covering the needle, or removing the needle, which requires two hands All of these designs require at least two hands to operate. The use of two hands to cover the contaminated needle is most unsatisfactory in that during the act of placing a second hand on the vial filling device or syringe, the person holding the vial filling device or syringe in one hand may be bumped and accidentally inject the needle into their other hand before it can grasp the syringe or vial filling device. Other accidental jabbing or injections can happen in an ambulance where just as a person tries to grasp the contaminated vial filling device or syringe, the ambulance can hit a bump in the road causing the person holding the vial filling device or syringe to accidentally stick another person or themselves with the contaminated needle. The need has developed for a vial filling device or syringe that will cover the contaminated needle with the use of only one hand.

SUMMARY

It is the object of this invention to provide a vial filling device wherein the needle of the vial filling device is retracted into the barrel of the vial filling device and protects others from an accidental pricking after it has been used; the needle cannula can be retracted into the barrel with the use of only one hand and that one hand being the hand that was used to inject the needle cannula into a vial and vial plug.

Another object of the present invention is to render the vial filling device useless after the needle cannula is retracted into the barrel of the vial filling device to prevent the accidental reuse of the contaminated vial filling device.

It is still another object of the present invention to further prevent the accidental release of the needle cannula after the needle cannula is in the barrel of the vial filling device.

The foregoing and other objects and advantages are attained by a vial filling device, comprising an elongated hollow barrel, a needle cannula, spring, slidable piston, and lapping flange in combination with a latching means wherein when said vial filling device is used to thrust a needle cannula through the soft plug at one end of the vial by pushing on the thumb flat with the thumb and forcing the slidable piston to push the needle cannula through the soft plug until the point of the needle cannula penetrates the soft plug and allows blood or other fluid to flow into the vial at one end of the vial soft plug by pressing on the thumb flat with the thumb and forcing the slidable piston to push the needle cannula through the soft plug until the point of the needle cannula penetrates the soft plug and allows blood or other fluid to flow into the vial for testing purposes. When the vial is filled, the thumb is removed from the thumb flat and the spring further pushes the needle cannula fixed to the slidable piston into the elongated hollow barrel of the vial filling device rendering the contaminated needle harmless to prevent the accidental pricking of others and to prevent a contaminated needle from being released from the elongated hollow barrel of the vial filling device.

The features of the present invention can be best understood together with further objects and advantages by reference to the following descriptions taken in connection with accompanying drawing, wherein like numerals indicate like parts.

BRIEF DESCRIPTION OF THE DRAWINGS

FIG. 4 is a section view of the needle cannula penetrating the vial plug.

FIG. 5 is an enlarged view taken through FIG. 1.

FIG. 6 is a section taken through FIG. 1.

FIG. 10 is a section elevation showing the needle cannula being disposed of.

DETAILED DESCRIPTION OF THE PREFERRED EMBODIMENTS

Figure 1:
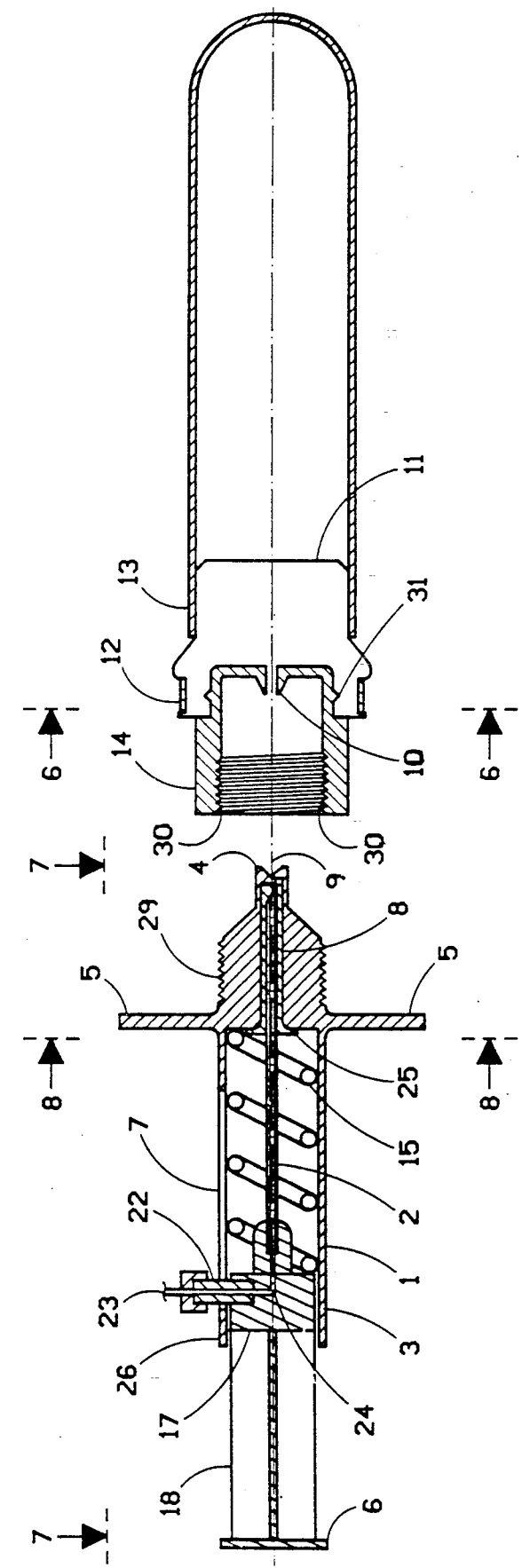
FIG. 1 is a section elevation view of the preferred embodiment of the present invention.

Referring to FIG. 1 there is shown a vial filling device 1, prior to insertion into plug fitting 14 that is fixed to the vial 13.

The vial filling device 1 is comprised of an elongated hollow barrel 3 with a slot 7 on one side of the elongated hollow barrel 3. The slot 7 is shown more clearly in FIG. 7. At the first end of the elongated hollow barrel 3 there is shown a slidable piston 17 and at the second end of the elongated hollow barrel there is further shown a lap flange 4. The elongated hollow barrel is also shown with two finger flanges 5 that will be held or gripped by fingers when the vial 13 is being filled.

The slidable piston 17 is shown with a piston shaft 18 at the first end and a needle cannula 2 fixed to the second end. The piston shaft 18 is shown fixed to the slidable piston at the second end of the piston shaft 18 and a thumb flat 6 at the first end of the piston shaft 18.

An open spring 15 is shown pushing the slidable piston 17 away from the barrel flange 25 of the elongated hollow barrel 3. As the spring 15 pushes on the slidable piston 17 the slidable piston 17 is restrained from being pushed out of the elongated hollow barrel 3 by the stop fitting 22. The stop fitting 22 is shown inserted into the slidable piston 17 at the first end and attached to a fluid tube 23 at the second end. The stop fitting 22 is further restraining the slidable piston 17 from being pushed out of the elongated hollow barrel by the barrel wall 26 at the end of the slot 7.

A cannula 24 or tunnel is shown in the slidable piston 17. The cannula 24 or tunnel connects the cannula of the fluid tube 23 and the cannula of the stop fitting with the cannula or tunnel of the needle cannula 2.

The needle cannula 2 is shown extending from the second end of the slidable piston 17 to a point at the second end of the needle cannula near the lap flange 4. The lap flange 4 prevents the point of the needle cannula 2 from accidentally being pushed out of the elongated hollow barrel 17. Fluid is prevented from flowing out of the needle cannula 2 and into the elongated hollow barrel 3 and onto the spring 15 and out of the elongated hollow barrel 3 by the needle cannula seal 8 that fits around the point and opening of the needle cannula 2.

The plug fitting 14 is made of a material that is harder than the soft rubber or plastic plug 11. The plug fitting is inserted into a cutout formed in plug 11 and then the plug band 12 is placed around the circumference at the first end of the plug 11 and tightened until the plug 11 squeezes the plug fitting 14 and further locks the plug fitting 14 to the plug 11. The plug fitting 14 is also held more firmly by the plug fitting ridge 31 that extends around the circumference near the second end of the plug fitting 14.

The plug fitting threads 30 are shown on the plug fitting 14 and they will correspond with the elongated hollow barrel threads 29. This will allow the elongated hollow barrel 3 to be suitably fastened to the vial 13 as will be shown in FIG. 3.

When the elongated hollow barrel 3 is screwed into the plug fitting 14 the concave annulus 9 will be forced into the convex annulus 10 thus forcing the convex annulus 10 and the lap flange 4 to open for the needle cannula 2 to pass through.

Figure 2:
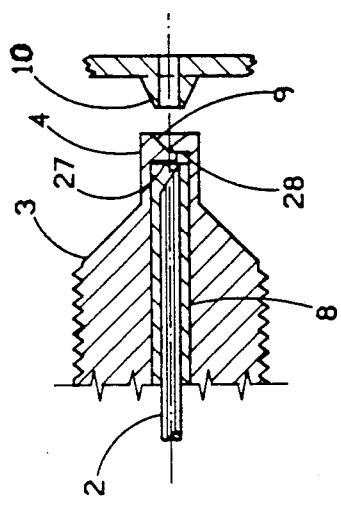
FIG. 2 is a section elevation detail of the lap flange of the embodiment showing the lap flange prior to opening.

Referring to FIG. 2 there is shown an enlarged section view of the concave annulus 9 and the convex annulus 10.

The lap flange 4 is shown closed. The inner flange 27 is shown lapping over the outer flange 28. With the lap flange 4 in a closed position, the needle cannula cannot open the lap flange 4 or go through the lap flange 4, because the point of the needle cannula cannot spread the lap flange apart. To open the lap flange, the convex annulus 10 must be pushed into the concave annulus 9 to suitably spread the concave annulus apart to allow the needle cannula's 2 passage through the lap flange 4.

Also shown in FIG. 2 is the needle cannula seal 8 in the elongated hollow barrel 3.

Figure 3:
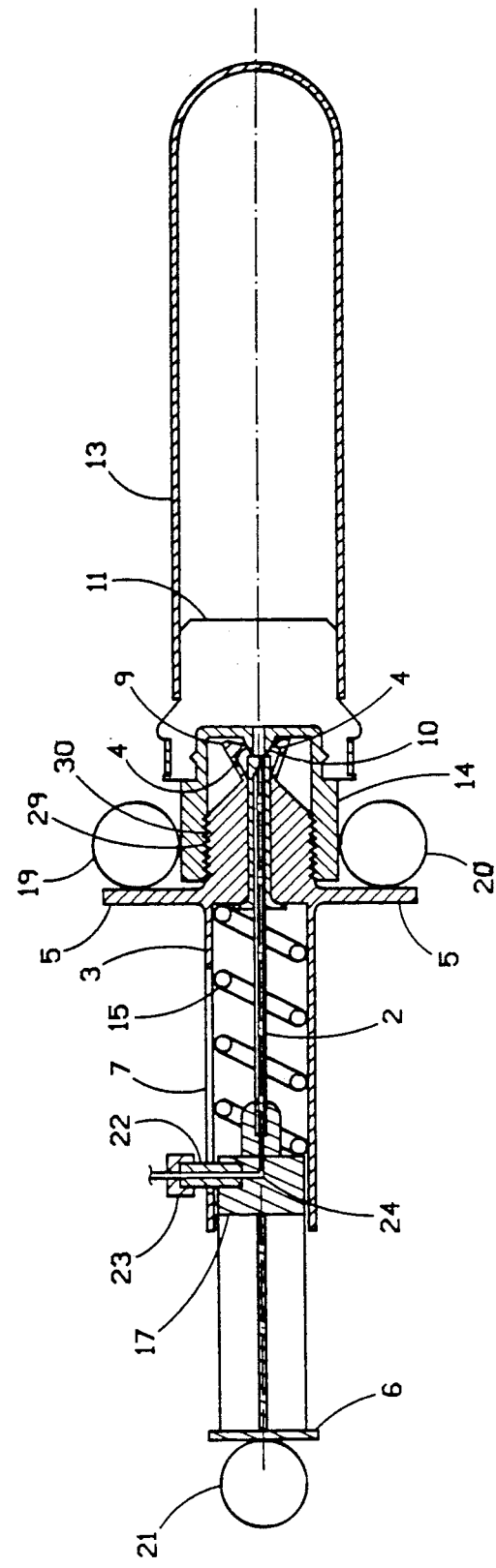
FIG. 3 is a section elevation view of the preferred embodiment showing the elongated hollow barrel attached to the vial.

Referring to FIG. 3 there is shown the elongated hollow barrel 3 suitably fastened to the plug fitting 14 by the elongated hollow barrel threads 29 on the elongated hollow barrel 3 and the plug fitting threads 30 on the plug fitting 14. The stop fitting 22 is shown in the slot 7. The slidable piston 17 is shown held in place by the spring 15.

As the elongated hollow barrel 3 is screwed onto the plug fitting 14 the convex annulus 10 is forced into the concave annulus 9 forcing open the lap flange 4.

To hold the elongated hollow barrel 3 and the vial 13, finger 19 and finger 20 are place on the finger flanges 5 and the thumb 21 is placed on the thumb flat 6.

The blood or fluid may already be in the fluid tube 23, the cannula 24, and the needle cannula 2 ready to flow into the vial 13 with a vacuum.

Referring to FIG. 4 there is shown the thumb 21 pushing on the thumb flat 6 which pushes on the piston shaft 18 and the slidable piston 17 and the needle cannula 2 forcing the needle cannula 2 through the soft plug 11 and further causing the second end of the needle cannula 2 to enter the vial that may have a vacuum. The slidable piston 17 also pushes and compresses the spring 15. The spring is compressed against the second end of the slidable piston 17 and the elongated hollow barrel flange 32. The stop fitting 22 has moved in the slot 7 in the direction of the vial 13.

Referring to FIG. 5, there is shown an enlarged section elevation of a portion of FIG. 4.

The needle cannula 2 has penetrated the soft plug 11 and blood or other fluid would be flowing into the vial 13. The second end of the soft plug 11 is shown inserted into the vial 13. The second end of the plug fitting 14 is shown inserted into the first end of the soft plug 14 and it is held in pace within the recess in the soft plug 11 by the plug band 12 compressing the soft plug around the plug fitting 14 and the plug fitting ridge 31.

The elongated hollow barrel 3 is shown screwed into plug fitting 14. As the elongated hollow barrel 3 is screwed into the plug fitting 14 the convex annulus 10 forces open the concave annulus 9 until the lap flange 4 is open sufficiently to allow the needle cannulas 2 to pass into the soft plug 11.

Referring back to FIG. 3, after sufficient blood or fluid has flowed into the vial 13, the thumb 21 is pulled back some or removed from the thumb flat 6 and the spring 15 pushes or thrusts on the slidable piston 17 until the stop fitting 22 reaches the end of the slot 7; the force or thrust of the spring 15 on the slidable piston 17 withdraws the needle cannula 2 from the soft plug 11 until the second end of the needle cannula 2 is past the lap flange 4 of the elongated hollow barrel 3.

Referring back to FIG. 1, after the needle cannulas 2 is withdrawn from the soft plug 11 and the second end of the needle cannulas 2 is withdrawn past the lap flange 4 as stated earlier, the elongated hollow barrel 3 is unscrewed or disengaged from the plug fitting 14, the lap flange 4 closes again. The material that the lap flange 4 is made from is sufficiently resilient to close the lap flange 4 once the convex annulus 10 is removed from the concave annulus 9.

Referring to FIG. 6 there is shown a section view as taken through FIG. 1.

The plug band 12 is shown wrapped around the soft plug 11 and the plug fitting 14 is shown held in the soft plug 11.

The nut 33 and bolt 34 are used to tighten the plug band 12 however another suitable means may be used to tighten the plug band 12 around the soft plug 11.

Figure 7:
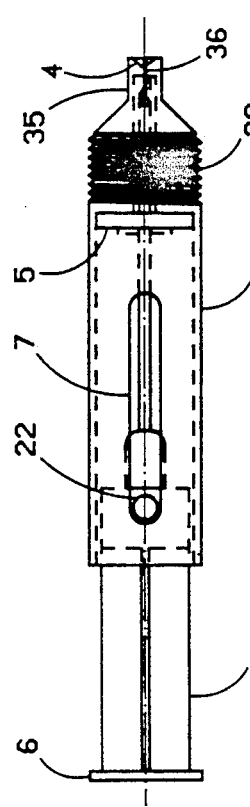
FIG. 7 is an elevation of the elongated hollow barrel as taken through FIG. 1.

Referring to FIG. 7 there is shown an elevation of the elongated hollow barrel 3.

The slot 7 is shown with stop fitting 22 in the first end of the slot 7. The thumb flat 6 is shown on the piston shaft 18 that is projecting from the first end of the elongated hollow barrel 3. The finger flanges 5 are shown near the second end of the elongated hollow barrel 3.

The elongated hollow barrel threads 29 are shown and the lap flange neck 35 is also shown at the second end of the elongated hollow barrel 3. A lap flange slot 36 is shown in the lap flange neck 35. There are two to four lap flange slots 36 that will allow the lap flange 4 to open and to close without breaking the lap flange neck 35. The lap flange neck 35 should be made out of a suitable resilient material that will allow the lap flange to open and close without breaking.

Figure 8:
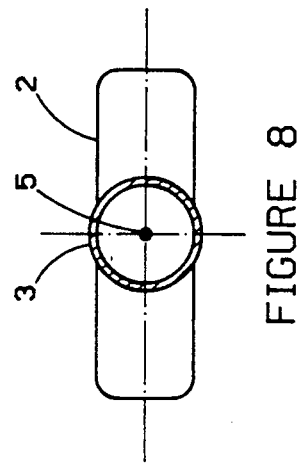
FIG. 8 is a section as taken through FIG. 1.

Referring to FIG. 8 there is shown a section view as taken through FIG. 1 of the finger flanges 5 that are fixed to the elongated hollow barrel 3. The needle cannula 2 is shown in the center of the elongated hollow barrel 3.

Figure 9:
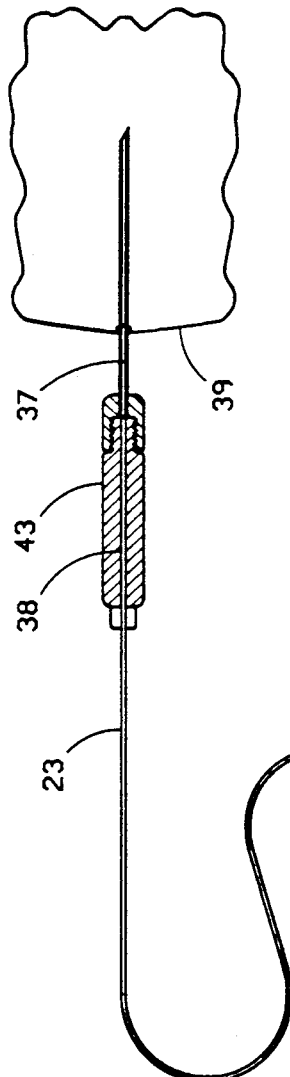
FIG. 9 is a section elevation of the preferred embodiment attached to a blood sampling device.
Figure 9:
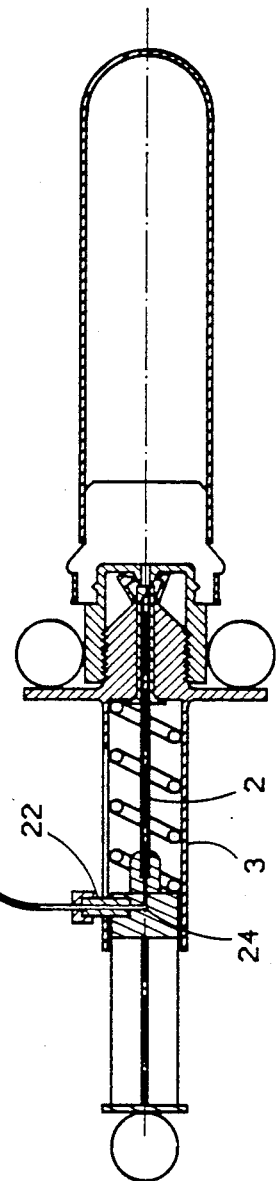

Referring to FIG. 9 there is shown a blood sampling device 43 with a blood sampling needle cannula 37 in a body 39.

The blood or fluid enters the blood sampling needle cannula 37 and flows through the blood sampling cannula 38 where it further flows into the tube 23 through the stop fitting 22, through the cannula 24 through the needle cannula 2 and into the vial 13.

Figure 10:
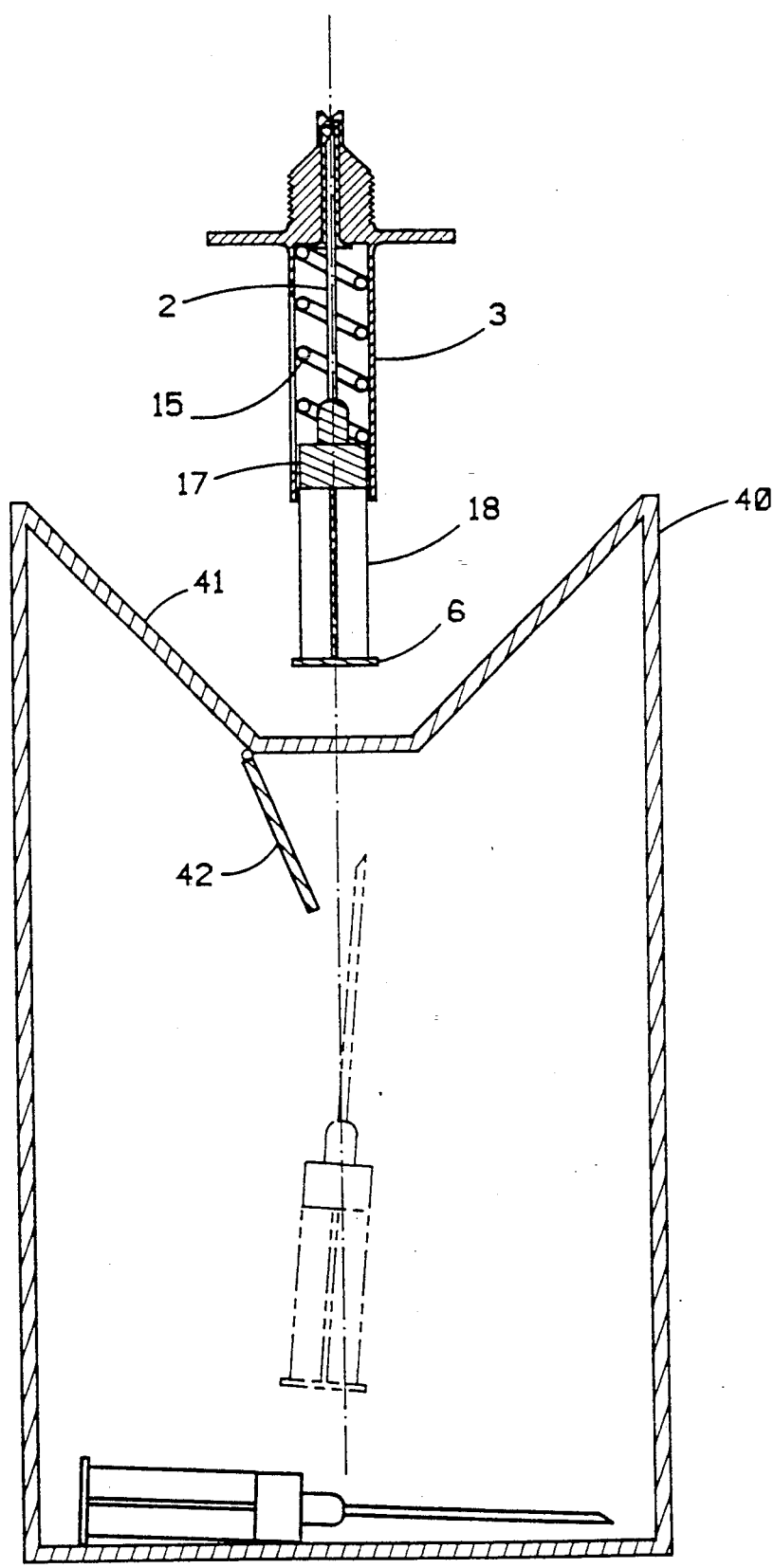

Referring to FIG. 10, there is shown a means of dumping the thumb flat 6, the piston shaft 18, the slidable piston 17, and the needle cannula 2 into a safety container 40.

The stop fitting is removed from the slidable piston 17 thus freeing the slidable piston 17 within the elongated hollow barrel 3. The elongated hollow barrel 3 is then turned over. When the elongated hollow barrel 3 is turned over, the slidable piston 17, the thumb flat 6, the piston shaft 18, and the needle cannula 2 fall out into a safety container 40 with a funnel top 41 that will guide the slidable piston 17 and the needle cannula 2, etc. into the safety container 40. At the bottom of the funnel top 41 is a safety door 42 that will close if the safety container is accidentally turned over, thus preventing the contaminated needle cannula 2 from falling out. When the slidable piston 17 and the needle cannula 2, etc are dumped into the safety container 40, they do not have to be touched and may be disposed of in the proper manner. The elongated hollow barrel 3 and the spring 15 may be reused after they have been suitably sterilized.

Although the system described in detail supra has been found to be most satisfactory and preferred many variations are possible. For example, the vial filling device may have two or more lap flanges, the vial filling device could be square in section or the stop fitting could be placed closer to the needle cannula.

Although the invention has been described with reference to the preferred embodiment, it will be understood by those skilled in the art, that additions, modifications, substitutions, deletions, and other changes not specifically described, may be made in the embodiments herein, it should be understood that the details herein are to be interpreted as illustrative and are not in a limiting sense.

What is claimed as invention is:

1. A vial filling device for inserting a needle cannula through a plug in the vial wherein blood or other fluid flows into the vial comprising:

an elongated hollow barrel having a first end and a second end;

a barrel flange formed near the second end of said elongated hollow barrel;

a slidable piston inside of said elongated hollow, said slidable piston having a first end and a second end;

a needle cannula with a first end and a second end. Said first end of said needle cannula is fixed to said second end of said slidable piston;

a spring disposed between said second end of said slidable piston and said barrel flange;

a piston shaft with a thumb flat at the first end of said piston shaft and said piston shaft is further fixed to said slidable piston at the second end of said piston shaft;

a lap flange at the second end of said elongated hollow barrel, said lap flange having a first side and a second side, said first side is perpendicular to said needle cannula;

a concave annulus disposed on said second side of lap flange;

a plug having a first end and a second end, said plug is fixed to said vial at said second end of said plug;

a plug fitting with a first end and a second end, said plug fitting is fixed to said first end of said plug at said second end of said plug fitting;

a convex annulus fixed to said plug fitting and wherein said second end of elongated hollow barrel is attached to said second end of said plug fitting, pushing said concave annulus into said convex annulus thereby forcing said lap flange open to further allow said second end of said needle cannula to pass said lap flange and to further extend through said plug wherein said second end of said needle cannula is inserted into said vial wherein said blood or fluid flows through said needle cannula into said vial and wherein said spring will further thrust said slidable piston toward said second end of said elongated hollow barrel, pulling said needle cannula out of said vial and plug and further enclosing said needle cannula within said elongated hollow barrel and wherein said elongated hollow barrel is disengaged with said plug fitting and said vial and wherein said concave annulus is disengaged with said convex annulus thereby allowing said lap flange to close wherein said needle cannulus is trapped within said elongated hollow barrel and said lap flange cannot extend out of said elongated barrel.

2. The vial filling device of claim 1 wherein a needle cannulus seal is disposed in said second end of said elongated hollow at the said second end of said needle cannulus covering the second end of said needle cannulus to further prevent the spilling of blood or fluid before said needle cannulus is inserted into said vial and after said needle cannulus is withdrawn from said vial.

3. The vial filling device of claim 1 wherein said elongated hollow barrel has at least one slot in one side of said elongated hollow barrel.

4. The vial filling device of claim 3 wherein a stop fitting is inserted into said slidable piston and said stop fitting extends out of said slidable piston and further extends through said slot.

5. The vial filling device of claim 1, wherein said elongated hollow barrel further has a thread near said second end of said elongated hollow barrel and said plug fitting further has a thread inside of said plug fitting that is compatible with said thread at the said second end of said elongated hollow barrel for allowing said elongated hollow barrel to be securely fastened to said plug fitting.

6. The vial filling device of claim 1, wherein said lap flange has a lap flange neck and said lap flange neck is made out of resilient material that can be expanded and will contract when the said concave annulus is withdrawn from the said convex annulus 7. The vial filling device of claim 6, wherein said flange neck has at least one flange neck slot formed into said flange neck, said flange neck slot will further allow said lap flange to open and close.

8. The vial filling device of claim 1, wherein said elongated hollow barrel may be inverted over a safety container and said slidable piston and said needle cannula will fall out of said elongated hollow barrel and will further fall into said safety container.

9. The vial filling device of claim 1, wherein said plug fitting is fixed to said plug by plug band on the outside of said plug wherein said plug band compresses the said plug around the said plug fitting.

* * * * *